(12) United States Patent
Shalev et al.

(10) Patent No.: US 7,922,761 B2
(45) Date of Patent: Apr. 12, 2011

(54) ARTIFICIAL VASCULAR PROSTHESIS

(75) Inventors: Alon Shalev, RaAnana (IL); Alexander Dubson, Petach-Tikva (IL)

(73) Assignee: Nicast Ltd., Lod (IL)

( * ) Notice: Subject to any disclaimer, the term of this patent is extended or adjusted under 35 U.S.C. 154(b) by 626 days.

(21) Appl. No.: 11/795,917

(22) PCT Filed: Jan. 25, 2006

(86) PCT No.: PCT/IL2006/000102
§ 371 (c)(1),
(2), (4) Date: Jul. 24, 2007

(87) PCT Pub. No.: WO2006/080008
PCT Pub. Date: Aug. 3, 2006

(65) Prior Publication Data
US 2008/0208316 A1    Aug. 28, 2008

Related U.S. Application Data

(60) Provisional application No. 60/646,542, filed on Jan. 25, 2005.

(51) Int. Cl.
*A61F 2/06* (2006.01)

(52) U.S. Cl. ............................... 623/1.44; 623/1.41
(58) Field of Classification Search ........ 623/1.32–1.48; 424/426, 443
See application file for complete search history.

(56) References Cited

U.S. PATENT DOCUMENTS

| | | | | |
|---|---|---|---|---|
| 4,816,339 A * | 3/1989 | Tu et al. | ......... | 428/421 |
| 5,716,394 A * | 2/1998 | Bruchman et al. | ......... | 623/1.44 |
| 6,054,122 A * | 4/2000 | MacPhee et al. | ......... | 424/94.4 |
| 6,440,166 B1 * | 8/2002 | Kolluri | ......... | 623/1.4 |
| 6,645,518 B2 * | 11/2003 | Tedeschi et al. | ......... | 424/423 |
| 7,056,412 B2 * | 6/2006 | Henderson | ......... | 156/294 |
| 7,118,592 B1 * | 10/2006 | Dang et al. | ......... | 623/1.12 |
| 7,452,374 B2 * | 11/2008 | Hain et al. | ......... | 623/1.44 |
| 7,615,373 B2 * | 11/2009 | Simpson et al. | ......... | 435/398 |
| 7,699,890 B2 * | 4/2010 | Yan | ......... | 623/1.44 |
| 2004/0018226 A1 * | 1/2004 | Wnek et al. | ......... | 424/443 |
| 2004/0054406 A1 | 3/2004 | Dubson et al. | | |
| 2006/0020328 A1 * | 1/2006 | Tan | ......... | 623/1.42 |
| 2006/0149358 A1 * | 7/2006 | Zilla et al. | ......... | 623/1.22 |

* cited by examiner

*Primary Examiner* — Suzette J Gherbi
(74) *Attorney, Agent, or Firm* — Browdy and Neimark, PLLC

(57) ABSTRACT

A vascular prosthesis having a tubular structure is provided. The tubular structure is fabricated from at least two layers wherein at least one layer includes a thrombogenic agent.

26 Claims, 2 Drawing Sheets

ARTIFICIAL VASCULAR PROSTHESIS

RELATED APPLICATIONS

This Application is a National Phase of PCT Patent Application No. PCT/IL2006/000102 having International Filing Date of Jan. 25, 2006, which claims the benefit of U.S. Provisional Patent Application No. 60/646,542 filed on Jan. 25, 2005. The contents of the above Applications are all incorporated herein by reference.

FIELD AND BACKGROUND OF THE INVENTION

The present invention relates to a vascular prosthesis having self sealing capabilities and, more particularly, to vascular grafts fabricated from non-woven materials impregnated or coated with thrombogenic agents.

End-stage renal disease (ESRD) occurs when the kidneys are no longer able to function at a level that is necessary for day to day life. It usually occurs as chronic renal failure worsens to the point where kidney function is less than 10% of normal. At this point, the kidney function is so low that without dialysis or kidney transplantation, complications are multiple and severe, and death will occur from accumulation of fluids and waste products in the body. The most common cause of ESRD in the U.S. is diabetes.

Patients suffering from end stage renal disease typically undergo artificial dialysis of their blood, as a substitute to kidney transplantation. In the U.S. more than 400,000 people are on long-term dialysis and more than 20,000 have a functioning transplanted kidney.

Dialysis filters a patient's blood and rids the body of harmful wastes and extra salt and fluids. It also controls blood pressure and helps the body maintain the proper balance of chemicals such as potassium, sodium, and chloride.

Two common types of dialysis are employed, peritoneal dialysis and hemodialysis. In hemodialysis, the blood is filtered through an artificial kidney machine. Peritoneal dialysis uses a filtration process similar to hemodialysis, but the blood is filtered inside the body rather than by an external machine.

Hemodialysis is typically performed three times a week. Each treatment lasts from 2 to 4 hours and necessitates vascular access, typically to a major artery and a major vein of the patient.

There are three basic kinds of vascular accesses for hemodialysis, an arteriovenous (AV) fistula, an AV graft, and a venous catheter. A fistula is an opening or connection between any two parts of the body that are usually separate, for example, a hole in the tissue that normally separates the bladder from the bowel. While most kinds of fistula are a problem, an AV fistula is useful because it causes the vein to grow large and strong for easy access to the blood system. The AV fistula is considered the best long-term vascular access for hemodialysis because it provides adequate blood flow for dialysis, lasts a long time, and has a complication rate lower than the other access types. If an AV fistula cannot be created, an AV graft or venous catheter may be needed.

The current standard artificial vascular graft is fabricated from extruded expanded polytetrafluoroethylene ("ePTFE"). Such a ePTFE graft typically requires 2-4 weeks to mature following implantation and prior to initial use. Additionally, ePTFE grafts take 10-15 minutes to achieve hemostasis following puncture for hemodialysis. Another disadvantage with ePTFE vascular prostheses is suture-hole bleeding. This problem ahs been partially resolved by devising a special suture device (i.e. the "Goretex Suture") whose suture is thicker than its introducing needle.

Several vascular access grafts have been devised in efforts of traversing sealing limitations inherent to vascular grafts. The VascuLink™, or Expedial™ produced by LeMaitre Vascular are two examples of such grafts. These devices are fabricated from enforced polycarbonate urethane foam. Although LeMaitre Vascular claims that these devices minimize suture hole bleeding, at present, clinical data demonstrating superior performance of these devices is unavailable.

A promising manufacturing technique of vascular prostheses is electrospinning.

Electrospinning creates a fine stream or jet of liquid that upon proper evaporation of a solvent or liquid to solid transition state yields a non-woven structure. The fine stream of liquid is produced by pulling a small amount of polymer solution through space by using electrical forces. More particularly, the electrospinning process involves the subjection of a liquefied substance, such as polymer, into an electric field, whereby the liquid is caused to produce fibers that are drawn by electric forces to an electrode, and are, in addition, subjected to a hardening procedure. In the case of liquid which is normally solid at room temperature, the hardening procedure may be mere cooling; however other procedures such as chemical hardening (polymerization) or evaporation of solvent may also be employed. The produced fibers are collected on a suitably located precipitation device and subsequently stripped therefrom. The sedimentation device is typically shaped in a desired geometry of the final product, which may be for example tubular in the case of vascular grafts.

The use of electrospinning for manufacturing or coating of vascular prostheses permits to obtain a wide range of fiber thickness (from tens of nanometers to tens of micrometers), achieves exceptional homogeneity, smoothness and desired porosity distribution along the coating thickness. When a graft includes an electrospun layer having a porous structure, such pores are invaded by cells and biologically active molecules from the region of the artery surrounding the graft.

The present inventors have previously demonstrated the advantages of using electrospinning for generating vascular grafts (see for example, International Patent Application, Publication Nos. WO 2002/049535, WO 2002/049536, WO 2002/049536, WO 2002/049678, WO 2002/074189, WO 2002/074190, WO 2002/074191, WO 2005/032400 and WO 2005/065578).

While reducing the present invention to practice and in efforts of improving self-sealing properties of vascular grafts the present inventors have devised a vascular graft which includes a layer impregnated or coated with a thrombogenic agent which substantially reduces bleeding from suture or needle access holes.

SUMMARY OF THE INVENTION

According to one aspect of the present invention there is provided a vascular prosthesis having a tubular structure comprising at least two layers wherein at least one layer of the at least two layers includes a thrombogenic agent.

According to another aspect of the present invention there is provided a method of fabricating a vascular prosthesis comprising: (a) depositing a first material onto a template to thereby form a first layer; and (b) depositing a second material composed from or including a thrombogenic agent onto the first layer to thereby form the vascular prosthesis.

According to further features in preferred embodiments of the invention described below, the method further comprises depositing a third layer onto the second layer following step (b).

According to still further features in the described preferred embodiments the depositing of step (a) and/or step (b) is effected via electrospinning. According to still further features in the described preferred embodiments the template is a mandrel. According to still further features in the described preferred embodiments the mandrel is sized and configured for fabrication of a vascular access graft.

According to still further features in the described preferred embodiments the first and/or the second material is a polymer.

According to still further features in the described preferred embodiments the first layer is characterized by porosity suitable for cellular seeding.

According to still further features in the described preferred embodiments the method further comprises removing the vascular prosthesis from the template.

According to yet another aspect of the present invention there is provided a method of providing vascular access for a dialysis patient comprising connecting a lumen of an artery and a vein of the patient via the artificial graft described herein.

According to still further features in the described preferred embodiments the thrombogenic agent is coated upon or impregnated within a non-inner layer of the at least two layers.

According to still further features in the described preferred embodiments a liner layer of the at least two layers is configured having a porosity suitable for cellular seeding.

According to still further features in the described preferred embodiments at least one layer of the at least two layers is fabricated from a non-woven polymeric fiber.

According to still further features in the described preferred embodiments at least one layer of the at least two layers is fabricated from an electrospun material.

According to still further features in the described preferred embodiments the tubular structure is sized and dimensioned for use as a vascular access graft.

According to still further features in the described preferred embodiments the vascular prosthesis further comprises a support structure.

According to still further features in the described preferred embodiments the support structure extends along said prosthesis.

According to still further features in the described preferred embodiments the support structure is embedded in the tubular structure.

According to still further features in the described preferred embodiments the thrombogenic agent is thrombin. According to still further features in the described preferred embodiments the thrombogenic agent is selected from the group consisting of platelet activating factor or an analogue thereof, collagen, fibrin, factor V, factor IX, an Antiphospholipid antibody or a portion thereof, copper or an alloy thereof and platinum or an alloy thereof.

According to still further features in the described preferred embodiments the tubular structure further comprises reinforcing fibers having a diameter selected from a range of 10 to 1000 micrometers.

According to still further features in the described preferred embodiments the tubular structure further comprises reinforcing fibers having a diameter selected from a range of 300 to 500 micrometers.

According to still further features in the described preferred embodiments a layer of the at least two layers is fabricated from the thrombogenic agent.

The present invention successfully addresses the shortcomings of the presently known configurations by providing a vascular access graft exhibiting superior self sealing capabilities.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
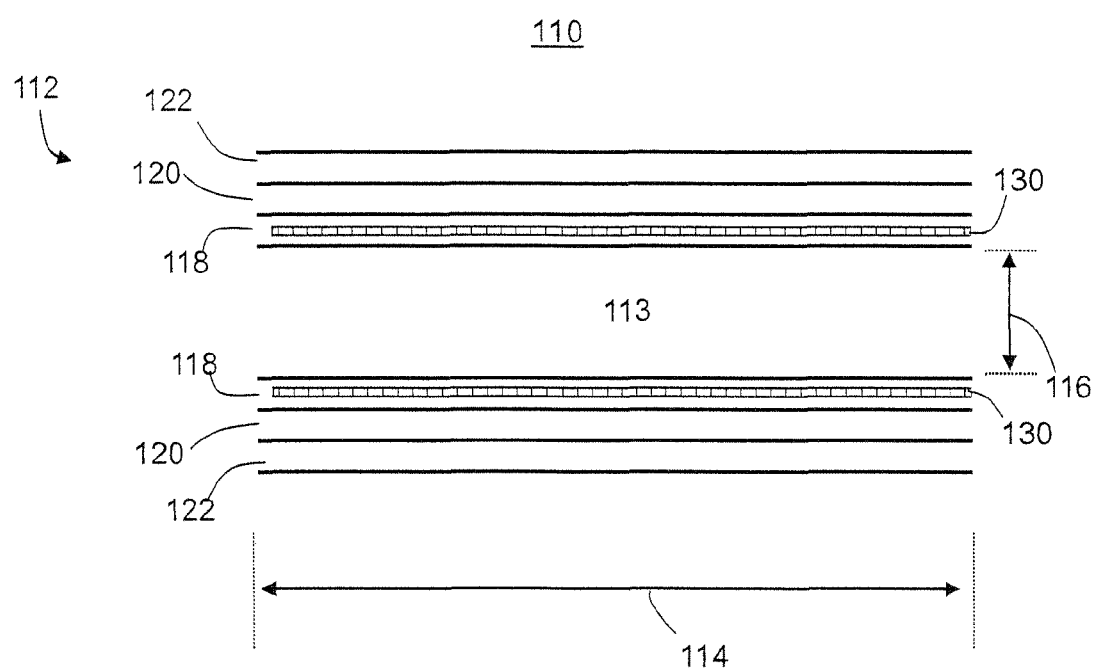
FIG. 1 illustrates a vascular prosthesis fabricated in accordance to the teachings of the present embodiments.

The present embodiments comprise a vascular prosthesis which can be used as a vascular access graft. Specifically, the present embodiments can be used to provide a vascular access graft which includes self sealing capabilities and thus minimizes suture and needle puncture leaks.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Numerous types of synthetic vascular prosthesis are known in the art. Although the problem of suture and needle hole sealing has been addressed in some prior art prosthesis designs, there remains a need for a synthetic vascular access graft which can be sutured into place and repeatedly penetrated by a needle without appreciably leaking blood. The graft must preferably also be utilizable shortly following implantation in a subject in need of such a graft.

While reducing the present invention to practice, the present inventors have devised a synthetic graft configuration which overcomes the limitations of prior art grafts and provides a self sealing graft wall which can be sutured into place and utilized for vascular access (e.g., in hemodialysis) shortly following implantation.

Thus, according to one aspect of the present invention, there is provided a vascular prosthesis which can be used as a vascular access graft, a vascular shunt such as an arteriovenous shunt, a replacement for blood vessel, a bypass vascular prosthesis and the like.

As used herein, the term vascular prosthesis refers to any tubular structure which is suitable for use, for example, as a vascular graft.

The vascular prosthesis of the present embodiments is a tubular structure which is fabricated from at least two layers, preferably, three or more layers.

As used herein, the term "tubular" refers to any tube-like structure having walls defining a lumen and having a constant or variable diameter throughout its length.

The vascular prosthesis of the present embodiments can be fabricated at any size and configuration depending on the intended purpose. For example, when utilized as a vascular access graft, the tubular structure is fabricated having a length of from about 1 cm to about 50 cm and an internal diameter of from about 1 mm to about 30 mm, more preferably from about 2 mm to about 20 mm, most preferably from about 2 mm to about 6 mm. The wall thickness of the tubular structure is preferably from about 20 µm to about 2 mm, more preferably from about 30 µm to about 1 mm.

As used herein the term "about" refers to ±10%.

The vascular prosthesis of the present embodiments is preferably characterized by enhanced physical, mechanical and biological properties. Without limitation, the properties are any combination of the following characteristics: (a) inner diameter expandable by at about 10% under a pulsatile pressure characterizing a mammalian blood system; (b) capable of maintaining the inner diameter while bent at a bent diameter of 150% said inner diameter; (c) having a porosity of at least 60%; (d) preventing leakage of blood passing therethrough; (e) characterized by tissue ingrowth and cell endothelization over at least 90% of the vascular prosthesis within at least 10 days from implantation in a mammal; and (f) having a self-sealing properties so as to minimize blood leakage following piercing.

As is mentioned hereinabove, the tubular structure of the vascular prosthesis of the present embodiments is fabricated from 2 or preferably 3 or more (e.g., 4 or 5) layers. Each such layer serves a specific function in the prosthesis. For example, an inner layer, e.g., the liner layer (defining the lumen), is typically designed such that it promotes cell seeding (for endothelialization), while one or more outer layers are designed for providing the graft with radial and longitudinal tensile strengths and self sealing capabilities. Thus, the present embodiments provide a composite tubular structure which promotes long term function of the graft by providing a cell seeding inner layer while exhibiting radial tensile by using one or more outer layers.

It has been shown that tubular structures having pores greater than 40 microns promote cell endothelialization along the inner blood contacting surface, while tubes having pores less than 40 microns exhibit inferior healing characteristics, but offer superior radial tensile strength and suture retention resilience, both being traits which are highly desirable in a vascular graft. Thus, to facilitate cell seeding (either in-vivo or in-vitro), the inner layer of the composite tubular structure of the vascular graft of the present embodiments include pores which are at least 40 microns in diameter, while a radial and longitudinal tensile strengths of the composite tubular structure is provided by one or more outer layers having pores smaller than 40 microns.

The vascular graft of the present invention can be fabricated from a biodegradable, a biostable polymer or a combination of a biodegradable and a biostable polymer. According to a preferred embodiment of the present invention the vascular graft of the present invention is formed of an elastomer.

Suitable biostable polymers which can be used in the present embodiments include, without limitation, polycarbonate based aliphatic polyurethanes, silicon modified polyurethanes, polydimethylsiloxane and other silicone rubbers, polyester, polyolefins, polymethyl-methacrylate, vinyl halide polymer and copolymers, polyvinyl aromatics, polyvinyl esters, polyamides, polyimides and polyethers.

Suitable biodegradable polymers which can be used in the present embodiments include, without limitation, poly(L-lactic acid), poly(lactide-co-glycolide), polycaprolactone, polyphosphate ester, poly(hydroxy-butyrate), poly(glycolic acid), poly(DL-lactic acid), poly(amino acid), cyanocrylate, some copolymers and biomolecules such as collagen, DNA, silk, chitosan and cellulose.

While woven or extruded-foam tubular structure are suitable for use in vascular grafts, the present inventor has postulated that a fibrous structure, specifically of an inner layer of a non-woven (preferably electrospun) vascular prosthesis could provide, while using suitable polymers and process parameters, an exceptionally good interface for physiological integration between an artificial vascular prosthesis and biologic vasculatures. Moreover, providing lumen thickness and other physical parameters of the electrospun vascular prosthesis are carefully selected, an electrospun vascular graft would have some inherent self-sealing properties, due to the elasticity of the micrometric or sub-micrometric arrangement of the elastomeric matrix.

Thus, the vascular graft of the present embodiments is preferably fabricated using an Electrospinning approach. The Electrospinning steps may be performed using any Electrospinning apparatus known in the art. Suitable Electrospinning techniques are disclosed, e.g., in International Patent Application, Publication Nos. WO 2002/049535, WO 2002/049536, WO 2002/049536, WO 2002/049678, WO 2002/074189, WO 2002/074190, WO 2002/074191, WO 2005/032400 and WO 2005/065578, the contents of which are hereby incorporated by reference. Other spinning techniques are disclosed, e.g., U.S. Pat. Nos. 3,737,508, 3,950,478, 3,996,321, 4,189,336, 4,402,900, 4,421,707, 4,431,602, 4,557,732, 4,643,657, 4,804,511, 5,002,474, 5,122,329, 5,387,387, 5,667,743, 6,248,273 and 6,252,031 the contents of which are hereby incorporated by reference.

Although an artificial electrospun vascular graft could be endothelialized, and thus provide haemostatic properties when punctured, as well as low thrombogenicity and high resistance to stenosis, physiological endothelialization progresses at a rate of approximately 1 mm/day, implying that for a 20 cm graft, complete endothelialization could take around a year.

To minimize leakage from needle puncture holes prior to graft endothelialization, the present inventor has devised a graft which includes one or more layers containing a thrombogenic agent, such that upon needle extraction, a localized coagulation process would be triggered at the periphery of the needle hole, thereby enhancing the self sealing properties of an electrospun artificial vascular graft.

The thrombogenic agent is utilized in the graft to clot and seal leakage of blood through the wall of the graft. Although any layer of the tubular structure can be provided with such a thrombogenic agent, exposure of blood flowing through the vascular graft to the thrombogenic agent can lead to undesirable clotting as well as attenuation of any endothelialization and as such, the thrombogenic agents is preferably provided in or on a non-luminal layer (i.e., a layer disposed outside the layer defining the lumen of the tubular structure).

It is recognized that bleeding is prevented by platelets adhesion, aggregation and formation of the polymerized fibrin matrix at the site of vascular injury. The endothelial surface on the vessel wall is not thrombogenic. Vascular wall injury results in exposure of collagen and subendothelial proteins. The adherence of platelets to collagen is recognized as a critical initial event for generation of a haemostatic plug. The reason being the capturing of platelets from the flowing blood via rapid bond formation between their glycoprotein 1b receptor and von Willibrand factor immobilized on collagen.

In parallel with the platelets adhesion process, coagulation is initiated through release of tissue factor from the damaged vessel wall. Propagation of blood coagulation occurs by localized enzymatic complexes assembled on the plasma membrane of adherent platelets that expose negatively charged phospholipids. The thrombin thus formed further activates platelets and stabilizes the growing thrombus by the formation of fibrin.

Both platelets that are in direct contact with subendothelial collagen and platelets that form the main body of an adherent platelets thrombus can participate in the clot formation. The direct contact platelets are activated by collagen as well as by soluble agonists (such as thrombin). On the other hand, the platelets of the main body of the thrombus are activated by soluble agonists, with minimal or no collagen impact. According to a preferred embodiment of the present invention the thrombogenic agent is selected to affect the first phase of the thrombus formation so as to create weak clot formation and to occlude the holes in the artificial vessel.

Additional thrombogenic agents can be, for example, thrombin, a platelet activating factor or an analogue thereof, fibrin, factor V, factor IX, an antiphospholipid antibody or a portion thereof, copper or an alloy thereof, platinum or an alloy thereof a positively charged polymer (voltage being in the range between 0.2 and 0.8 volts), polyvinyl acrylate and cyanoacrylate.

Such agents are readily available in active or precursor form from a variety of suppliers. For example, thrombin or prothrombin can be obtained from Sigma-Aldrich.

According to presently preferred embodiments of the present invention, the thrombogenic agent is collagen (available from Sigma and BD Biosciences), von Willebrand Factor (preferably from a human source from HTI and American Diagnostica), thrombospondin (available from ProSpecTany TechnoGene and Sigma), tissue factor (available from Dade Behring and American Diagnostica), or various phospholipids (e.g. L-alpha Phosphatidylcholine, L-alpha-Phosphatidylserine, L-alpha-Phosphatidylethanolamine available from Avanti polar lipids)

To enable clotting of suture holes and more importantly of needle entry holes over a period of 12 months, the vascular graft of the present embodiments preferably includes a minimum recommended surface concentration of the thrombogenic agent per unit area of graft wall. Representative examples of preferred surface concentrations include, without limitation, from about 1 to about 20 $pg/mm^2$ foer for collagen, from about 1 to about 20 $pg/mm^2$ von Willebrand Factor, from about 1 to about 100 $pg/mm^2$ for Thrombospondin, from about 0.1 to about 5 $pg/mm^2$ for Tissue Factor.

Several approaches can be used to provide the thrombogenic agents in the vascular graft of the present embodiments.

For example, any layer of the tubular structure can be coated or impregnated with such an agent prior to fabrication of the graft. Alternatively, a polymer utilized for fabricating any layer can be attached, impregnated or coated with the agent prior to polymerization. Further detail of various approaches suitable for coating, impregnating or modifying polymers with various agents can be found, for example, in WO 02/049536 and WO 02/49535, supra.

The vascular graft of the present embodiments can also include additional pharmaceutical agents selected in accordance with the application and expected pathology. For example, the implantation of the graft may result in disorders such as restenosis, stenosis and hyper cell proliferation, in the blood vessel being in contact with the prosthesis. The incorporated pharmaceutical agent can therefore be a medicament for treating such and other disorders. Additionally or alternatively, the incorporated pharmaceutical agent can be an imaging agent to enable post implantation imaging. The additional pharmaceutical agent can be coated upon, attached to or impregnated within any layer of the tubular structure.

FIG. 1 schematically illustrates a longitudinal cross sectional view of the vascular graft of the present embodiments which is referred to herein as graft 110. Graft 110 comprises a walled tubular structure 112 having a lumen 113 characterized by a length (as indicated by numeral 114) and an average inner diameter (as indicated by numeral 116). Tubular structure 112 is preferably fabricated from three or more layers. In the exemplary embodiment of FIG. 1, tubular structure 112 comprises a liner layer 118, a middle layer 120 and a cover layer 122.

It is to be understood that the number of layers illustrate in FIG. 1 is not to be considered as limiting. Specifically, liner layer 118 can be replaced by two or more inner layers, middle layer 120 can be replaced by two or more intermediate layers and cover layer 122 can be replaced by two or more outer layer.

Liner layer 118 is preferably fabricated with porosity suitable for promoting cell seeding and endothelialization as described above, while cover layer 122 is preferably fabricated with porosity suitable for maintaining radial tensile strength. Intermediate layer 120 preferably includes the thrombogenic agent(s).

Optionally and preferably, graft 110 can also comprise a support structure 130, extending along the graft. Support structure 130 can be disposed internally within the tubular structure, or it can be embedded in the walls of the tubular structure (e.g., between to successive layers). Support structure 130 can be any support structure known in the art (to this end see, e.g., WO 02/49535 supra, and U.S. Pat. Nos. 6,945, 993, 6,949,120 and 6,939,373). For example, structure 130 can be a deformable mesh of wires made of a metallic material such as, but not limited to, medical grade stainless steel or a material exhibiting temperature-activated shape memory properties, such as Nitinol.

Thus, the present embodiment successfully provides a vascular prosthesis which can be combined with a support structure to create a "stent-graft" assembly, whereby which combines high mechanical strength and self-sealing properties. The advantage of such assembly is that it can be sutured to biological blood vessels while minimizing or preventing leakage due to the suturing procedure.

As is mentioned hereinabove, the vascular graft of the present embodiments is preferably fabricated using an Electrospinning approach.

Electrospinning may be performed using any electrospinning apparatus known in the art.

Figure 2:
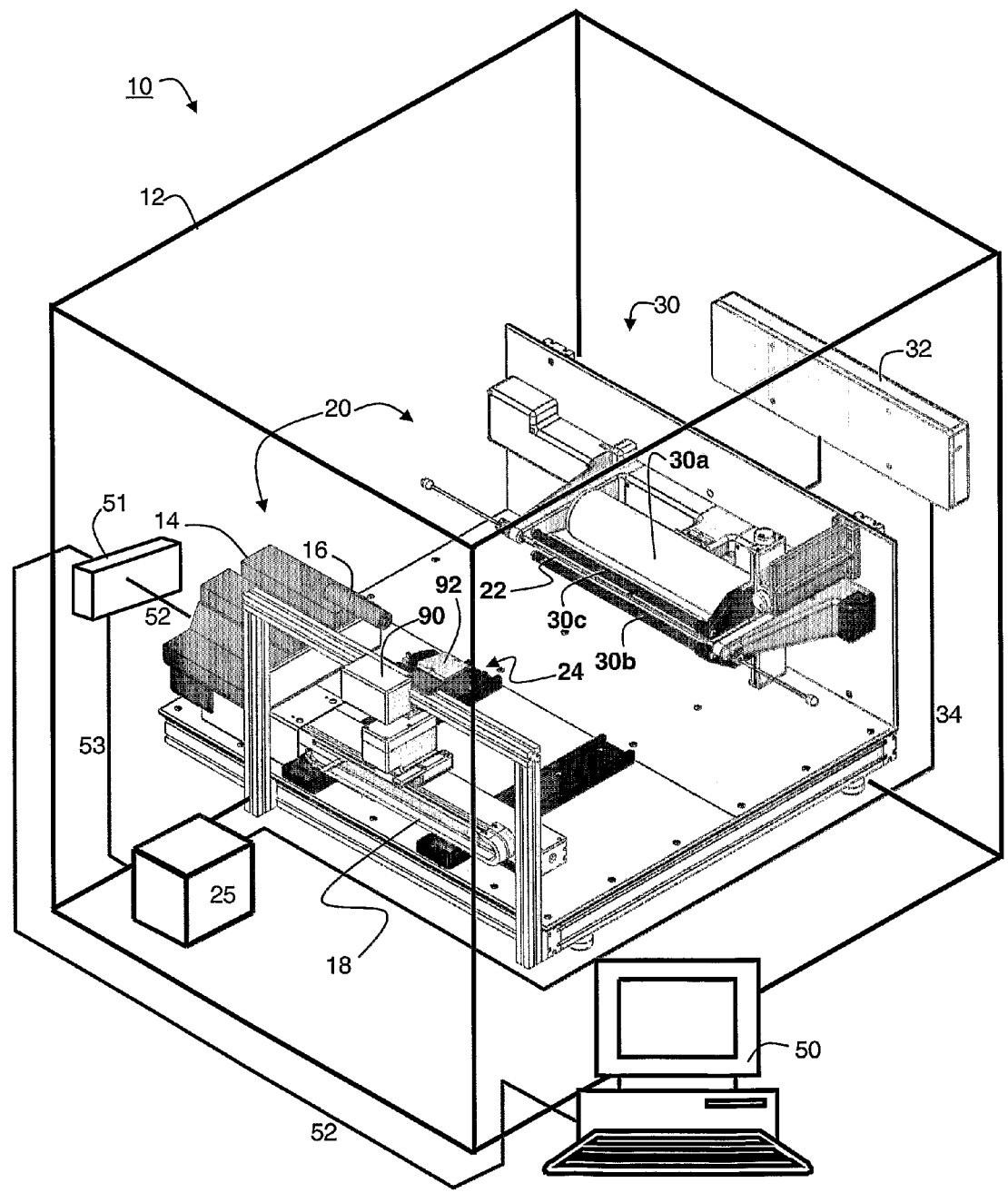
FIG. 2 illustrates an electrospinning system which can be utilized to fabricate the vascular prosthesis of the present embodiments.

FIG. 2 schematically illustrates a system 10 for manufacturing an vascular graft. In its simplest configuration, System 10 comprises an electrospinning system 20 having a precipitation electrode 22, and a dispenser 24, positioned at a predetermined distance from a precipitation electrode 22 and being kept at a first potential relative to precipitation electrode 22.

The potential difference between dispenser 24 and precipitation electrode 22 is preferably from about 10 kV to about 100 kV, typically about 60 kV. The potential difference between dispenser 24 and precipitation electrode 22 generate an electric field therebetween.

Dispenser 24 serves for dispensing a liquefied polymer in the electric field to produce polymer fibers precipitating on electrode 22. Precipitation electrode 22 serves for forming the vascular graft thereupon. Precipitation electrode 22 is typically manufactured in accordance with the geometrical properties of the final product which is to be fabricated. In various exemplary embodiments of the invention the vascular graft has a tubular shape and electrode 22 is in a form of a rotating mandrel. Electrode 22 can be made of, for example, stainless steel.

System 10 preferably comprises a subsidiary electrode system 30, which is preferably at a second potential relative to precipitation electrode 22 and configured to shape the aforementioned electric field. Typically, electrode system 30 is connected to source 25 by line 34 and a circuitry 32 which alters (typically reduce) the output voltage of 25 to the desired level. A typical potential difference between electrode 22 and electrode system 30 is from about 10 kV to about 100 kV, typically about 50 kV.

Electrode system 30 may comprise a plurality of electrodes in any arrangement. The size, shape, position and number of electrodes in system 30 is preferably selected so as to maximize the coating precipitation factor, while minimizing the effect of corona discharge in the area of precipitation electrode 22 and/or so as to provide for controlled fiber orientation upon deposition.

In the exemplified configuration shown in FIG. 2, which is not to be considered as limiting, system 30 comprises three cylindrical electrodes, designated 30a, 30b and 30c, where electrode 30a is of larger diameter and is positioned behind precipitation electrode 22, while electrodes 30b and 30c are of smaller diameter and poisoned above and below electrodes electrode 22.

Subsidiary electrode system 30 controls the direction and magnitude of the electric field between precipitation electrode 22 and dispenser 24 and as such, can be used to control the orientation of polymer fibers precipitated on electrode 22. In some embodiments, subsidiary electrode system 30 serves as a supplementary screening electrode. Generally, the use of screening results in decreasing the coating precipitation factor, which is particularly important upon cylindrical precipitation electrodes having at least a section of small radii of curvature.

Electrode shapes which can be used in the present embodiments include, but are not limited to, a plane, a cylinder, a torus a rod, a knife, an arc or a ring.

Specifically, a cylindrical or planar subsidiary electrode enables manufacturing intricate-profile products being at least partially with small (from about 0.025 millimeters to about 5 millimeters) radius of curvature. Such subsidiary electrodes are also useful for achieving random or circumferential alignment of the fibers onto precipitation electrode 22.

The ability to control fiber orientation is important when fabricating vascular grafts in which a high radial strength and elasticity is important. It will be appreciated that a polar oriented structure can generally be obtained also by wet spinning methods, however in wet spinning methods the fibers are thicker than those used by electrospinning by at least an order of magnitude.

Control over fiber orientation is also advantageous when fabricating composite polymer fiber shells which are manufactured by sequential deposition of several different fiber materials.

Subsidiary electrodes of small radius of curvature (e.g., electrodes 30b and 30c), can be used to introduce distortion the electric field in an area adjacent to precipitation electrode 22. For maximum effect the diameter of subsidiary electrode 26 must be considerably smaller than that of precipitation electrode 22, yet large enough to avoid generation of a significant corona discharge.

According to a preferred embodiment of the present invention system 10 the position of subsidiary electrode system 26 can be varied relative to precipitation electrode 22. Such design further facilitates the ability to control the electric field vector (intensity and direction) near electrode 22.

System 10 further comprises a compartment 12, encapsulating electrospinning system 20 and subsidiary electrode system 30. Preferably, but not obligatorily, compartment 12 also encapsulates source 25, and circuitry 32, including the connection lines. Compartment 12 is preferably made of a material being transmissive in the visual range, Compartment 12 serves for keeping a clean environment therein. According to a preferred embodiment of the present invention the clean environment is of class 1000 (i.e., less than one thousands particles larger than 0.5 microns in each cubic foot of space) or cleaner. More preferably the clean environment is of class 100 (i.e., less than one thousand particles larger than 0.5 microns in each cubic foot of air space).

More specifically, compartment 12 serves as a climate chamber which besides the clean environment, maintains therein predetermined levels of other environmental conditions such as temperature and humidity.

Thus, according to a preferred embodiment of the present invention the temperature with compartment 12 is kept at a predetermined constant level within an accuracy of ±1° C., more preferably ±0.5° C. even more preferably ±0.2° C., so as to control and maintain the desired evaporation rate during the electrospinning process. Maintenance of accurate temperature within compartment 12 is advantageous because the thickness of the produced polymer fibers and the porosity of the vascular graft, depends, inter alia, on the evaporation rate of solvent from the polymer jets emerge from dispenser 24. Preferred temperatures for the operation are from about 22° C. to about 40° C.

Additionally, the humidity within compartment 12 is maintained at a predetermined level to an accuracy of 5% more preferably 3% even more preferably 1%. Maintenance of accurate temperature within compartment 12 is useful for preventing or reducing formation of volume charge. Preferred humidity level, in relative value (the weight or pressure of moisture relative to the maximal weight or pressure of moisture for a given temperature) is about 40%.

Dispenser 24 and/or precipitation electrode 22 preferably rotates such that a relative rotary motion is established between dispenser 24 and electrode 22. Similarly, Dispenser 24 and/or electrode 22 preferably moves such that a relative linear motion is established between dispenser 24 and electrode 22. In the exemplified configuration shown in FIG. 2, precipitation electrode rotates without performing a linear motion, while dispenser 24 performs a linear motion without performing a rotary motion. However, this need not necessarily be the case, since, for some applications, it may be desired to rotate dispenser 24 about a longitudinal axis 21 of electrode 22 and/or to establish a linear motion of electrode 22 along its longitudinal axis.

When electrode 22 rotates about its axis, the rotation can be established by any mechanism, such as, but not limited to, an electrical motor, an electromagnetic motor, a pneumatic motor, a hydraulic motor, a mechanical gear and the like.

In various exemplary embodiments of the invention system 10 preferably comprises a data processor 50 supplemented by an algorithm for controlling the operation of electrospinning system 20. Data processor 50 can communicate with system 20 directly or through a control unit 51 located within compartment 12. The communication can be via communication line 52 or, more preferably, via wireless communication so as to preserve to clean environment in compartment 12. Preferably, but not obligatorily, processor 50 also communicates (e.g., through control unit 51 and communication line 53) with source 25 for controlling the aforementioned potential differences and for automatically activating and deactivating system 10. According to a preferred embodiment of the present invention processor 50 is configured (e.g., by a suitable computer program) to vary the relative rotary motion and/or relative linear motion between dispenser 24 and electrode 22. For example, when electrode 22 rotates by means of electric motor 40, the power supplied to motor 40, hence the angular velocity of electrode 22 is controlled by processor 50. Similarly, when dispenser 24 moves along convey 54 by means of electric motor 58, the power supplied to motor 58, hence the linear velocity of dispenser 24 is controlled by processor 50.

As will be appreciated by one ordinarily skilled in the art, different angular and/or linear relative velocities can result in different precipitation rates of polymer fibers on electrode 22. Thus, the computerized control on the motions can be used to select the desired precipitation rate, hence also the desired wall thickness of the vascular graft.

Additionally, processor 50 can signal the mechanism for establishing the linear and/or angular motions of dispenser 24 and/or electrode 22 to change the corresponding velocities, at a given instant or instances of the process. This embodiment is particularly useful when manufacturing multilayer vascular grafts. Thus, by selecting different motion characteristics of dispenser 24 and/or electrode 22 for different layers, the electrospinning process for each layer is at a different precipitation rate, resulting in a different density of fibers on the formed layer. Since the porosity of the layer depends on the density of fiber, such process can be used for manufacturing multilayer vascular grafts in which the layers have predetermined and different porosities. Additionally, each layer can have a different wall thickness, which can also be controlled as further detailed above.

The graft of the present embodiments is preferably manufactured as follows.

One or more liquefied polymers are provided and introduced into the electrospinning system. The liquefied polymer(s) can also be mixed with one or more conductivity control agents or charge control agents for improving the interaction of the fibers with the electric field.

The distance between the precipitation electrode and the subsidiary electrodes, the distance between the dispenser and the precipitation electrode, and the angle between the dispenser and the precipitation electrode are adjusted by the adjustments mechanism and recorded into the data processor.

System 10 is sealed by the compartment and the appropriate environmental conditions are established. Parameters, such as, but not limited to, wall thickness, number of layer, angular and linear velocities, temperature, hydrostatic pressure, polymer viscosities, and the like, are recorded into the data processor. Also recorded are the types of polymers.

System 10 is activated and the liquefied polymer is extruded under the action of the hydrostatic pressure through the spinnerets. As soon as meniscus of the extruded liquefied polymer forms, a process of solvent evaporation or cooling starts, which is accompanied by the creation of capsules with a semi-rigid envelope or crust. Because the liquefied polymer possesses a certain degree of electrical conductivity, the capsules become charged by the electric field. Electric forces of repulsion within the capsules lead to a drastic increase in hydrostatic pressure. The semi-rigid envelopes are stretched, and a number of point micro-ruptures are formed on the surface of each envelope leading to spraying of ultra-thin jets of the liquefied polymer from the spinnerets.

Under the effect of a Coulomb force, the jets depart from the dispenser and travel towards the opposite polarity electrode, i.e., the precipitation electrode. Moving with high velocity in the inter-electrode space, the jet cools or solvent therein evaporates, thus forming fibers which are collected on the surface of the precipitation electrode.

Once a first layer is formed, the data processor signals the dispenser to reselect a different liquefied polymer (in embodiments in which different liquefied polymers are used for different layers), and the motion mechanisms to change the rotary and/or linear velocities (in embodiments in which different the layers have different wall thicknesses and/or different porosities). The signaling of the data processor is preferably performed without ceasing the electrospinning process, such that the new layer is formed substantially immediately after the previous layer.

Once all the layers are formed, the compartment is opened and the precipitation electrode, including the vascular graft formed thereupon is disengaged from the system.

According to a preferred embodiment of the present invention the removal of the electrospun product from the precipitation electrode is preferably performed as follows. The precipitation electrode, including the vascular graft, is irradiated by ultrasound radiation. It was found by the inventor of the present invention that ultrasound radiation facilitates the removal of the vascular graft from the electrode. Additionally and more preferably, the precipitation electrode including the vascular graft can also be subjected to at least one substantially abrupt temperature change. The abrupt temperature change can be applied by any suitable heat carrier, including, without limitation, a liquid bath. The removal process can also be controlled by the data processor. Specifically, the data processor can control the duration and level of the applied temperatures and/or the ultrasound radiation.

The process of removal can thus be performed in accordance with various exemplary embodiments of the invention as follows. The precipitation electrode including the vascular graft is immersed in an ultrasonic bath of low temperature (about 0° C.) for a first predetermined period (about 1-10 minutes, more preferably 3-5 minutes). Subsequently, the precipitation electrode including the vascular graft is immersed in another ultrasonic bath of high temperature (from about 40° C. to about 100° C.) for a second predetermined period (about 1-10 minutes, more preferably 3-5 minutes). In experiments performed by the present inventor it was found that the vascular graft can then be removed from the precipitation electrode by an easy manual effort.

If a vascular prosthesis fabricated using the above described procedure requires additional radial strength, radial reinforcing fibers or wires can be added during or following electrospinning. The reinforcing fibers preferably have a diameter from about 300 micrometers to about 500 micrometers.

The advantage of using the electrospinning method for fabricating vascular prosthesis is flexibility of choosing the polymer types and fibers thickness, thereby providing a final product having the required combination of strength, elastic and other properties as delineated herein. In addition, an alternating sequence of the layers, each made of differently oriented fibers, determines the porosity distribution nature along the vascular prosthesis wall thickness. Electrospinning method also has the advantage of allowing the incorporation of thrombogenic agents as well as various pharmaceutical agents into the fibers by dissolving such agents in the liquefied polymers prior to electrospinning. The examples section which follows provides further detail with respect to fabrication of a thrombin-containing vascular graft.

A vascular graft fabricated according to the teachings of the present embodiments can be implanted in a subject in need utilizing any well known approach.

For example, the vascular graft is used as an access graft, e.g., an arteriovenous shunt, a pair of openings can be formed in an artery and a vein. Thereafter, the vascular graft can be connected to the pair of openings to allow blood flow from the artery through the vascular graft and into the vein.

When the vascular graft is used for replacing a portion of a blood vessel, the portion of the blood vessel can be excised to create a pair of blood vessel ends. Thereafter the vascular graft can be connected to the pair of blood vessel ends to allow blood flow through the graft.

When the vascular graft is used for bypassing, e.g., an obstructed portion of a blood vessel, forming a pair of openings can be formed in the blood vessel, upstream and downstream the obstruction. Thereafter, the vascular graft can be connected to the pair of openings to allow blood flow through the vascular graft.

It is expected that during the life of this patent many relevant polymeric material will be developed and the scope of the term polymer is intended to include all such new technologies a priori.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Materials, Devices and Methods

A silicon polycarbonate urethane copolymer CarboSil 20 was purchased from Polymer Technology Group Incorporated, and was used for graft manufacturing. This polymer has satisfactory fiber-generation abilities, it is biocompatibilty and is capable of lipophilic drug incorporation. A mixture of dimethylformamide and toluene of ratio ranging from 1:1 to 1:2 was used as a solvent in all experiments. For the formation of adhesive sublayers, polycarbonate urethane Chronoflex 80A was used.

A pump was purchased from Harvard Apparatus and was used in the electrospinning apparatus. For the dispensing electrode, three simultaneously operating spinnerets were used, mounted one above the other with a height of 20 mm therebetween. The inner diameter of the spinnerets was 0.5 mm. The flow-rate of each of the spinnerets was between 1 ml/h and 5 ml/h. The dispensing electrode was grounded while the precipitation electrode was kept at a potential of about 50 kV. The mandrel, made of polished stainless steel, was rotated at an angular velocity of 0.5-5 radians per second.

The dispensing electrode was positioned about 25 cm to 35 cm from the precipitation electrode and was connected to the pump with flexible polytetrafluorethylene tubes. Reciprocal motion of the dispensing electrode was enabled along the mandrel longitudinal axis at a frequency of 2÷3 motions/min. The longitudinal motion amplitude exceeded that of the manufactured graft by 10÷15%.

Example 1

A Two Layer Graft

A vascular prosthesis 6 mm in diameter and 200 mm in length was manufactured. A rod with 6 mm in diameter and 300 mm in length was used as a mandrel, and its central 200 mm portion was coated at ambient temperature, 24° C. Pump productivity was 3 ml/h.

CarboSil 20 polyurethane solution was used to form both the inner layer and the outer layer, the thickness of which was 80 μm and 720 μm respectively, hence the total wall thickness was 800 μm. In the inner layer, the viscosity of the solution was 450 cP and the conductivity was 0.45 μS, and in the outer layer, the viscosity was 680 cP and the conductivity 1.8 μS. The graft was removed from the mandrel, rinsed repeatedly in deionized water, dried and sterilized.

Results

The mechanical parameters of the graft according to ISO 7198:1998 (E), were: general porosity of 68%, kinking diameter of 30 mm and dynamic compliance of 9%.

Example 2

The Effect of Solution Viscosity

A vascular prosthesis 6 mm in diameter and 200 mm in length was manufactured as described in Example 1, however for both inner layer and outer layer equal solution viscosity of 450 cP and equal conductivity of 0.45 μS was used. In addition, the pump productivity was increased to 5 ml/h.

Results

The above changes lead to a slightly higher value of general porosity but lower anti-kinking strength and compliance. The mechanical parameters of the graft according to the ISO were: general porosity of 70%, kinking diameter of 35 mm and dynamic compliance of 8%.

Example 3

The Effect of a Predetermined Fiber Orientation

A vascular prosthesis 6 mm in diameter and 200 mm in length was manufactured, as in Example 2, with the outer layer being formed from fibers placed in transverse (polar)

orientation, for enhancing the radial strength of the graft. In addition, the thickness of the outer layer was 520 µm, hence total wall thickness reduced to 600 µm.

Results

The above changes lead to improvement of both antikinking resistance and dynamic compliance, without scarifying the general porosity. The mechanical parameters of the graft according to the ISO were: general porosity of 70%, kinking diameter of 32 mm and dynamic compliance of 10%.

Example 4

The Effect of Heating

A vascular prosthesis 6 mm in diameter and 200 mm in length was manufactured, as in Example 3, with the implementation of heating process as described herein. After the formation of the inner layer, an internal built-in Ohmic heater was employed so as to heat the mandrel and the inner layer to 70° C. The mandrel was kept in the above temperature throughout the process of outer layer formation.

Results

The heating of the mandrel after the formation of the inner layer resulted in a residual solvent drop from approximately 1200 ppm to 20 ppm. Low mass gain during the process ensured equal temperature of the mandrel and the outer layer. The heating process increased the porosity, the dynamic compliance and the antikinking resistance. The mechanical parameters of the graft according to the ISO were: general porosity of 78%, kinking diameter of 16 mm and dynamic compliance of 14%.

Example 5

A Multi Layer Graft with a an Additional Coiled Pattern

A vascular prosthesis 6 mm in diameter and 200 mm in length was manufactured. A rod 6 mm in diameter and a 300 mm in length was used as a mandrel, and its central 200 mm portion was coated at ambient temperature. Pump productivity was kept at 3 ml/h.

CarboSil 20 polyurethane solution was used to form the inner layer, the thickness of which was 80 µm. The viscosity of the solution was 450 cP and conductivity was 0.45 µS. Once the inner layer was formed, a 16 µm first intermediate layer of low hardness, highly elastic polyurethane Chronoflex 80A was applied. Then, a 0.3 mm polypropylene surgical thread was passed through a bath of Chronoflex 80A solution of 1500 cP viscosity, thereby forming a semi-solid polyurethane filament with a thickness of about 1 mm. Subsequently, the coated filament was wound around the intermediate layer, at a winding rate of 4.4 m/min, winding tension of 2 N and winding pitch of 1.1 mm.

Once the winding process was completed, a second intermediate layer, identical to the first intermediate layer, was applied. An outer layer, of 720 µm thickness was applied using CarboSil 20 polyurethane solution having a viscosity of 680 cP and conductivity of 1.8 µS.

Results

As the thread was utterly coated, an adhesion bond sufficient to prevent uncoiling was formed. The mechanical parameters of the graft according to the ISO were: general porosity of 64%, kinking diameter of 12 mm and dynamic compliance of 5%.

Example 6

The Effect of Using a Polymer Fiber Extruder

A vascular prosthesis 6 mm in diameter and 200 mm in length was manufactured as in Example 5, except that a polymer filament extruder was used to generate the filament, and no dipping process was employed. CarboSil 20 was used as a melt for the polymer fiber extruder, and a perfectly rounded filament, 0.32 mm in diameter, was generated. The filament was initially generated at a temperature of 195° C. and was subsequently cooled by airflow, hence the filament contacted the graft at a temperature of 130° C., ensuring adhesion of the filament to the graft. In this example, the winding pitch was 1.4 mm.

Results

The polymer filament extruder improved the dynamical compliance of the graft, leaving the other parameters unchanged. Hence, the mechanical parameters of the graft according to the ISO were: general porosity of 64%, kinking diameter of 12 mm and dynamic compliance of 10%.

A summary of the mechanical parameters of the above Examples is provided in Table 1.

TABLE 1

| | Example No. | | | | | |
|---|---|---|---|---|---|---|
| | 1 | 2 | 3 | 4 | 5 | 6 |
| Inner diameter [mm] | 6 | 6 | 6 | 6 | 6 | 6 |
| General porosity [%] | 68 | 70 | 70 | 78 | 64 | 64 |
| Kinking diameter [mm] | 30 | 35 | 32 | 16 | 12 | 12 |
| Dynamic compliance [%] | 9 | 8 | 10 | 14 | 5 | 10 |

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES

Zilla, et al, U.S. Pat. No. 6,702,848, "Foam-type vascular prosthesis with well-defined anclio-permissive open porosity", Mar. 9, 2004.

Zilla, et al., U.S. Pat. No. 6,616,699, "Foam-type vascular prosthesis with well-defined angio-permissive open porosity", Sep. 9, 2003.

Harris, et al., U.S. Pat. No. 6,589,278 "Vascular prosthesis", Jul. 8, 2003.

Schmitt et al., U.S. Pat. No. 5,697,969 "Vascular prosthesis and method of implanting", Dec. 16, 1997.

Miyake, et al., U.S. Pat. No. 5,584,877, "Antibacterial vascular prosthesis and surgical suture", Dec. 17, 1996.

Scopelianos, U.S. Pat. No. 5,522,879 "Piezoelectric biomedical device", Jun. 4, 1996.

Whalen, U.S. Pat. No. 5,354,329, "Vascular prosthesis having enhanced compatibility and compliance characteristics" Oct. 11, 1994.

Ostapchenko, U.S. Pat. No. 5,192,308 "Vascular prosthesis with an elastomer coating", Mar. 9, 1993.

Smith, U.S. Pat. No. 4,960,423, "Method of enhancing the attachment of endothelial cells on a matrix and vascular prosthesis with enhanced anti-thrombogenic characteristics", Oct. 2, 1990.

U.S. Pat. No. 4,941,870 to Okada, et al. Jul. 17, 1990, "Method for manufacturing a synthetic vascular prosthesis"

Okada et al., U.S. Pat. No. 4,878,907, "Synthetic vascular prosthesis", Nov. 7, 1989.

What is claimed is:

1. A vascular prosthesis having a tubular structure, comprising:
   a liner layer;
   a middle layer over the liner layer, including at least two layers wherein at least one layer of said at least two layers includes a thrombogenic agent;
   a cover layer over the middle layer; and
   a support structure,
wherein the support structure is between the liner layer and the middle layer, or between the middle layer and cover layer, or within one of the liner layer and middle layer, and said thrombogenic agent is impregnated within a non-inner layer of said at least two layers.

2. The vascular prosthesis of claim 1, wherein a liner layer of said at least two layers is configured having a porosity suitable for cellular seeding.

3. The vascular prosthesis of claim 1, wherein at least one layer of said at least two layers is fabricated from a non-woven polymeric fiber.

4. The vascular prosthesis of claim 1, wherein at least one layer of said at least two layers is fabricated from an electrospun material.

5. The vascular prosthesis of claim 1, wherein the tubular structure is sized and dimensioned for use as a vascular access graft.

6. The vascular prosthesis of claim 1, wherein said thrombogenic agent is collagen.

7. The vascular prosthesis of claim 1, wherein said thrombogenic agent is von Willebrand Factor.

8. The vascular prosthesis of claim 1, wherein said thrombogenic agent is Thrombospondin.

9. The vascular prosthesis of claim 1, wherein said thrombogenic agent is Tissue Factor.

10. The vascular prosthesis of claim 1, wherein said thrombogenic agent is a phospholipid.

11. The vascular prosthesis of claim 1, wherein said thrombogenic agent is selected from the group consisting of platelet activating factor or an analogue thereof, fibrin, factor V, factor IX, an Antiphospholipid antibody or a portion thereof, copper or an alloy thereof and platinum or an alloy thereof.

12. The vascular prosthesis of claim 1, wherein the tubular structure further comprises reinforcing fibers having a diameter selected from a range of 10 to 100 micrometers.

13. The vascular prosthesis of claim 1, wherein a layer of said at least two layers is fabricated from said thrombogenic agent.

14. The vascular prosthesis of claim 1, further comprising a support structure.

15. The vascular prosthesis of claim 14, wherein said support structure extends along said prosthesis.

16. The vascular prosthesis of claim 14, wherein said support structure is embedded in said tubular structure.

17. A method of fabricating a vascular prosthesis, comprising:
   (a) depositing a first material onto a template using a spinning method to thereby form a first layer;
   (b) depositing a second material composed from or including a thrombogenic agent onto said first layer using a spinning method to thereby form the vascular prosthesis; and
   (c) removing the vascular prosthesis from said template by ultrasound radiation, wherein the spinning method includes:
      mixing at least one liquefied polymer with at least one conductivity control agents or charge control agents;
      spraying jets of the liquefied polymer from a dispenser;
      forming fibers by evaporating a solvent in the jets of the liquefied polymer;
      collecting the fibers on the surface of the template; and
      rotating one of the template and the dispenser and linearly moving the other one of the template and dispenser simultaneously, thereby forming a porous layer on the template.

18. The method of claim 17, further comprising depositing a third layer onto said second layer following step (b).

19. The method of claim 17, wherein said depositing of step (a) and/or step (b) is effected via electrospinning.

20. The method of claim 17, wherein said template is a mandrel.

21. The method of claim 17, wherein said thrombogenic agent is thrombin.

22. The method of claim 17, wherein said thrombogenic agent is selected from the group consisting of platelet activating factor or an analogue thereof, collagen, fibrin, factor V, factor IX, an Antiphospholipid antibody or a portion thereof, copper or an alloy thereof and platinum or an alloy thereof.

23. The method of claim 17, wherein said first and/or said second material is a polymer.

24. The method of claim 20, wherein said mandrel is sized and configured for fabrication of a vascular access graft.

25. The method of claim 17, wherein said first layer is characterized by porosity suitable for cellular seeding.

26. The method of claim 17, further comprising removing the vascular prosthesis from said template.

* * * * *